United States Patent
Ichida

(10) Patent No.: US 7,081,548 B2
(45) Date of Patent: Jul. 25, 2006

(54) PROCESS FOR PREPARING 3-CHLORO-5-NITROTOLUENE

(75) Inventor: Akito Ichida, Aomori (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/727,317

(22) Filed: Dec. 3, 2003

(65) Prior Publication Data

US 2004/0147776 A1    Jul. 29, 2004

(30) Foreign Application Priority Data

Jan. 28, 2003  (JP)  ............................. 2003-018299

(51) Int. Cl.
*C07C 263/00*   (2006.01)
*C07C 205/00*   (2006.01)

(52) U.S. Cl. ...................... 560/347; 568/937
(58) Field of Classification Search ................ 560/347; 568/937
See application file for complete search history.

(56) References Cited

U.S. PATENT DOCUMENTS 3,523,964 A * 8/1970 Schnabel et al. ........... 560/342
3,972,910 A * 8/1976 Metzger et al. ............. 560/347

FOREIGN PATENT DOCUMENTS

JP     8-231489     9/1996
JP    08-231489     9/1996

OTHER PUBLICATIONS

Aldrich Catalogue, p. 1700, 1998-1999.*
XP-002275130, DE, English Abstract only.
XP-002275131, DE, English Abstract only.
XP-002275132, DE, English Abstract only.
3-Fluoro-, 3-chloro- and 3-bromo-5-methylphenylcarbamates of cellulose and amylose as chiral stationary phases for high-performance liquid chromatographic enantioseparation, by B. Chankvetadze et al, Journal of Chromatography, 1997, pp. 67-77.
"Synthesis and Structure—Activity Relationships of Chiral Allosteric Modifiers of Hemoglobin", by M. Grella, et al, J. Med. Chem., vol. 43, No. 25, 2000, pp. 4726-4737.
"A Convenient Procedure for the Chlorination of Deactivated Anilines", by Thomas E. Nickson, et al, Synthesis, 1985, pp. 669-670.
Synthesis and Structure—Activity Relationships of Chiral Allosteric Modifiers of Hemoglobin, by Melissa Phelps Grella et al, *J. Med. Chem.*, 2000, 43, 4726-4737.

* cited by examiner

*Primary Examiner*—Taylor Victor Oh
(74) *Attorney, Agent, or Firm*—Flynn, Thiel, Boutell & Tanis, P.C.

(57) ABSTRACT

A preparation process of 3-chloro-5-nitrotoluene is provided in mild conditions. It is a process for preparing 3-chloro-5-nitrotoluene, which involves the steps of reacting 2-methyl-4-nitroaniline with a chlorinating agent such as 5-butyl hypochlorite in a neutral condition to obtain 2-chloro-4-nitro-6-methylaniline and deaminating the 2-chloro-4-nitro-6-methylaniline to obtain 3-chloro-5-nitrotoluene.

6 Claims, No Drawings

PROCESS FOR PREPARING 3-CHLORO-5-NITROTOLUENE

FIELD OF ARTS OF THE INVENTION

The invention relates to a process for preparing 3-chloro-5-nitrotoluene and a process for preparing 3-chloro-5-methylphenylisocyanate.

PRIOR ARTS

JP-A 8-231489 and J. Med. Chem. 43, 4726–4737 (2000) show a process for preparing an isocyanate reacting with a polysaccharide and having a high separation power.

JP-A 8-231489 discloses a production process using potassium chloride in hydrochloric acid. The reference production process needs to be improved because a strong acid is used and a salt formed by neutralization of the product mixture has to be treated.

J. Med. Chem. discloses a reaction of 4-methyl-2-nitroaniline with N-chlorosuccinic imide. In the reference reaction, purification with column chromatography is necessary to separate the intended product from a side-produced succinic imide. It is not suitable for large-scale production.

SUMMARY OF THE INVENTION

The invention relates to a process for preparing 3-chloro-5-nitrotoluene in mild conditions, without any strong acid and any strong base, to obtain an isocyanate precursor, and then a process for preparing 3-chloro-5-methylphenylisocyanate, which is useful in producing an optical separation agent.

The invention provides, as means to solve the above shown problems, a process for preparing 3-chloro-5-nitrotoluene, which comprises reacting 2-methyl-4-nitroaniline with a chlorinating agent in a neutral condition to obtain 2-chloro-4-nitro-6-methylaniline and deaminating the 2-chloro-4-nitro-6-methylaniline to obtain 3-chloro-5-nitrotoluene.

The invention provides, as means to solve another problem, a process for preparing 3-chloro-5-methylphenylisocyanate, which comprises reducing 3-chloro-5-nitrotoluene obtained by the above shown process and reacting the resulting product with triphosgene.

DETAILED EXPLANATION OF THE INVENTION

The preparation of 3-chloro-5-nitrotoluene will be explained in line with the following reaction formula 1.

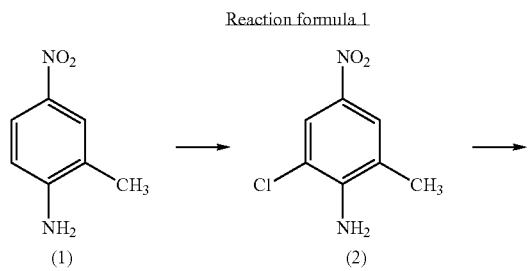

Reaction formula 1

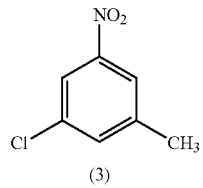

(3)

2-methyl-4-nitroaniline, (1) of the reaction formula 1, is first reacted with a chlorinating agent in a neutral condition to obtain 2-chloro-4-nitro-6-methylaniline, (2) of the reaction formula 1.

The reaction is preferably carried out in a solvent containing neither an acid nor a base at room temperature. The solvent is not particularly limited, as far as it is a solvent for both 2-methyl-4-nitroaniline and the chlorinating agent, and includes, for example, toluene, benzene, acetic acid, etc.

The chlorinating agent includes, for example, t-butylhypochlorite, N-chlorosuccinic imide, etc.

The reaction product of 2-chloro-4-nitro-6-methylaniline is isolated by filtering, etc., in advance to the subsequent reaction step. It may be washed or dried if necessary.

Then, 3-chloro-5-nitrotoluene, (3) of the reaction formula 1, is obtained from 2-chloro-4-nitro-6-methylaniline by deamination.

The deamination reaction for 2-chloro-4-nitro-6-methylaniline may proceed in a solvent such as ethanol or methanol. The reaction temperature is preferably controlled in plural steps in the following manner.

In the first step, the reaction mixture is adjusted between room temperature and 0° C., preferably 5 and 10° C., and then sodium nitrite is added thereto, preferably in the form of an aqueous solution of sodium nitrite of 1 to 2 mole equivalents.

In the second step, the reaction mixture is allowed to stand, preferably under stirring, at room temperature. It is observed that the temperature elevates up to about 45° C. by way of the reaction heat and then decreases down to lower than 40° C., then the reaction mixture is stirred at a temperature of 40 to 50° C. until no foaming occurs.

In the third step, the reaction mixture is cooled to room temperature and the reaction product is isolated by filtration or the like.

The preparation of 3-chloro-5-methylphenylisocyanate will be explained below in line with the following reaction formula 2.

Reaction formula 2

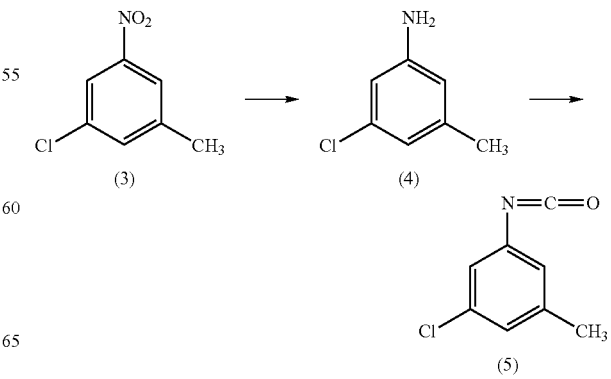

3-chloro-5-nitrotoluene, (3) of the reaction formula 2, is first dissolved in a solvent such as ethanol and the solution is reacted, while being cooled, with a reducing agent (a hydrogenating agent) such as tin chloride or Raney nickel to obtain 3-chloro-5-methylaniline, (4) of reaction formula 2.

Triphosgene is dissolved in a solvent such as toluene and 3-chloro-5-methylaniline and a toluene solution of triethylamine are added thereto at room temperature to react and obtain 3-chloro-5-methylphenylisocyanate, (5) of reaction formula 2.

3-chloro-5-nitrotoluene, obtained by the preparation of the invention, is useful as a precursor to 3-chloro-5-methylphenylisocyanate. 3-chloro-5-methylphenylisocyanate is useful in preparing conventional polysaccharides used as optical separating agents.

The process of the invention is carried out in mild conditions and suitable for large scale production.

EXAMPLE

The invention will be explained below by reference to examples. The invention, however, is not limited by the examples.

Example 1 preparation of 3-chloro-5-nitrotoluene

① preparation of 2-chloro-4-nitro-6-methylaniline 2-methyl-4-nitroaniline (56.0 g, 0.368 mol) was dispersed in toluene (430 ml) in a 1 liter four-neck flask. Tertiary butyl hypochloride (46.0 g, 0.423 mol) was added dropwise thereto, while cooled in iced water and stirred. The mixture was stirred at room temperature for 3 hours. The solids were filtered and washed three times with 200 ml of a 50% aqueous ethanol three times. They were then dried at 40° C. at a reduced pressure to obtain 55.33 g of a yellow solid (production yield 80%). The yellow solid was used in the subsequent step without purification.

$^1$H-NMR, 500 MHz, in $CDCl_3$ (δ)
8.12 (d, J=2.2 Hz, 1H)
7.92 (d, J=2.2 Hz, 1H)
4.73 (bs, 2H)
2.27 (s, 3H)

② preparation of 3-chloro-5-nitrotoluene 2-chloro-4-nitro-6-methylaniline (55.0 g, 0.295 mol) and ethanol (500 ml) were mixed in a 2 liter four-neck flask. A conc. Sulfuric acid (120 ml) was added dropwise to the reaction mixture at a temperature lower than room temperature. The reaction mixture was maintained at a temperature of 5 to 10° C. and an aqueous solution of sodium nitrite (26.44 g, 0.381 mol/40 ml) was added dropwise thereto over a period of 40 minutes.

The reaction mixture was then stirred at room temperature. It was observed that the temperature elevated up to 45° C. by way of the reaction heat and then decreased down to lower than 40° C. and then the reaction mixture was stirred at a temperature of 40 to 45° C. until no foaming occurred.

The product mixture was cooled to room temperature and poured into 2500 ml of iced water to obtain precipitates. They were filtered and dried at a reduced pressure to obtain 45.95 g of a yellow solid (production yield 90%).

$^1$H-NMR, 500 MHz, in $CDCl_3$ (δ)
8.03 (bs, 1H)
7.94 (bs, 1H)
7.50 (bs, 1H)
2.46 (s, 3H)

Example 2 preparation of 3-chloro-5-methylphenylisocyanate

① preparation of 3-chloro-5-methylaniline 3-chloro-5-nitrotoluene (45 g, 0.241 mol) and ethanol (500 ml) were mixed in a 2 liter four-neck flask. The mixture was cooled to about 4° C. A solution of tin chloride monohydrate (217.67 g, 0.965 mol) in 200 ml of ethanol was added dropwise to the mixture over 2 hours, while the reaction mixture was maintained at 10° C. or lower.

Then the reaction product mixture was stirred at room temperature for 2 hours and poured into 2500 ml of iced water. It was neutralized with sodium hydroxide and filtered with a nutsch filled with sellaite. The residue was washed with ethyl acetate. The intended product was obtained with ethyl acetate from the filtrate liquid.

Then the extract liquid and the washing liquid were joined. The mixture was washed with water and then saturated salt water and dried with magnesium sulfate. After being concentrated, it was treated by distillation at a reduced pressure to obtain 28.0 g of a yellow liquid (production yield 80%).

B.p.: 85–92° C./0.4 kPa or lower (3 Torr or lower)
$^1$H-NMR, 500 MHz, in $CDCl_3$ (δ)
6.56 (bs, 1H)
6.48 (dd, JI, J2=1.3 Hz, 1H)
6.36 (bs, 1H)
3.64 (bs, 2H)
2.22 (s, 3H)

② preparation of 3-chloro-5-methylphenylisocyanate

Triphosgene (17.01 g, 0.0573 mol) was dissolved in 200 ml of toluene in a 1 liter flask. 150 ml of a toluene solution of 3-chloro-5-methylaniline (21.9 g, 0.155 mol) and triethylamine (36.0 ml) was added dropwise thereto over 30 minutes at room temperature.

The reaction mixture was then stirred at 70° C. for 2 hours and cooled to room temperature. The obtained precipitates of hydrochloric acid salt of triethylamine were filtered out and the filtrate liquid was concentrated and treated with distillation at a reduced pressure to obtain 16.87 g of a colorless liquid (production yield 65%).

B.p.: 72–74° C./0.53–0.66 kPa (4–5 Torr)
$^1$H-NMR, 500 MHz, in $CDCl_3$ (δ)
7.00 (bs, 1H)
6.90 (bs, 1H)
6.80 (bs, 1H)
2.31 (s, 3H)

The invention claimed is:
1. A process for preparing 3-chloro-5-nitrotoluene, which comprises the steps of reacting 2-methyl-4-nitroaniline with t-butylhypochlorite in a neutral condition and in a solvent containing neither an acid or a base to obtain 2-chloro-4-nitro-6-methylaniline and deaminating a reactant mixture containing the 2-chloro-4-nitro-6-methylaniline by adding sodium nitrite to the reactant mixture adjusted to a temperature between room temperature and 0° C., allowing the reaction mixture to stand at an elevated temperature and then decreasing the temperature and maintaining the temperature at 40 to 50° C. to obtain 3-chloro-5-nitrotoluene.

2. A process for preparing 3-chloro-5-methylphenylisocyanate, which comprises the steps of reacting 2-methyl-4-nitroaniline with t-butylhypochlorite in a neutral condition to obtain 2-chloro-4-nitro-6-methylaniline and deaminating a reactant mixture containing the 2-chloro-4-nitro-6-methylaniline to obtain 3-chloro-5-nitrotoluene, reducing the 3-chloro-5-nitrotoluene with a reducing agent to obtain a resultant product and reacting the resultant product with triphosgene.

3. The process as claimed in claim 2, wherein the reducing agent is selected from the group consisting of tin chloride and Raney nickel.

4. The process as claimed in claim 2, wherein the reaction of 2-methyl-4-nitroaniline with t-butylhypochlorite is carried out in a solvent containing neither acid nor base and the deamination is carried out by adding sodium nitrite to the reactant mixture adjusted to a temperature between room temperature and 0° C., allowing the reaction mixture to stand at an elevated temperature and then decreasing the temperature and maintaining the temperature at 40 to 50° C.

5. The process as claimed in claim 1, wherein the solvent is toluene.

6. The process as claimed in claim 4, wherein the solvent is toluene.

* * * * *